United States Patent
Saïed et al.

(10) Patent No.: US 6,923,767 B2
(45) Date of Patent: Aug. 2, 2005

(54) SCANNING SYSTEM ALONG AN ARCIFORM TRAJECTORY WITH A VARIABLE BENDING RADIUS

(75) Inventors: Amena Saïed, Paris (FR); Arnaud Petetin, Saint Pierre en Faucigny (FR); Pascal Laugier, Paris (FR); Geneviève Berger, Bourg-la-Reine (FR); José Oliviera Sousa, Mery sur Oise (FR); Bernard Audenard, Orgeval (FR)

(73) Assignee: Quantel Medical (FR)

( * ) Notice: Subject to any disclaimer, the term of this patent is extended or adjusted under 35 U.S.C. 154(b) by 57 days.

(21) Appl. No.: 10/430,095

(22) Filed: May 6, 2003

(65) Prior Publication Data
US 2003/0220572 A1 Nov. 27, 2003

(30) Foreign Application Priority Data
May 7, 2002 (FR) .......................................... 02 05780

(51) Int. Cl.⁷ ................................................ A61B 8/00
(52) U.S. Cl. ............................ 600/445; 600/452; 74/25
(58) Field of Search .................................. 600/440, 447, 600/450–452; 74/25–69

(56) References Cited

U.S. PATENT DOCUMENTS

| | | | |
|---|---|---|---|
| 4,756,313 A | | 7/1988 | Terwilliger |
| 4,897,015 A | * | 1/1990 | Abbe et al. ............... 414/744.8 |
| 4,967,752 A | | 11/1990 | Blumenthal et al. |
| 5,167,165 A | | 12/1992 | Brucher et al. |
| 5,331,962 A | | 7/1994 | Coleman et al. |
| 5,487,388 A | | 1/1996 | Rello et al. |
| 5,587,637 A | * | 12/1996 | Ohyama ................ 318/568.11 |
| 5,632,703 A | * | 5/1997 | Wilkes et al. ................ 475/211 |
| 5,765,444 A | * | 6/1998 | Bacchi et al. ................ 414/783 |
| 5,944,476 A | * | 8/1999 | Bacchi et al. ................ 414/783 |
| 6,491,637 B2 | * | 12/2002 | Foster et al. ................. 600/452 |

FOREIGN PATENT DOCUMENTS

WO     WO 01 49181 A1     11/2002

* cited by examiner

Primary Examiner—Francis J. Jaworski
(74) Attorney, Agent, or Firm—William A. Drucker (57) ABSTRACT

The scanning system of the invention includes a structure driven in rotation around a first axis, a structuremounted rotating on the structure around an axis parallel to the first axis, a structure for supporting an echographic probe mounted rotating on the structure around a third axis parallel to the axis, a coupling element between the structure and the structure and a coupling element between the support structure and the structure. This system being able to move the probe along a variable band arciform trajectory.

20 Claims, 4 Drawing Sheets

— Ratio 1
—·— Ratio 1,1

FIG.9

— Ratio 1
—·— Ratio 1,1

SCANNING SYSTEM ALONG AN ARCIFORM TRAJECTORY WITH A VARIABLE BENDING RADIUS

BACKGROUND OF THE INVENTION

1. Field of the Invention

The present invention concerns a system for scanning along an arciform trajectory with a variable bending radius.

It can be applied especially, but not exclusively, to the echography of ocular structures, it being understood that it can also be used for guiding miscellaneous tools or instruments, both in the medical field and for controlling and machining spherical or aspheric materials having a convex or concave geometry.

2. Description of the Prior Art

In ultrasonic imagery and more particularly in medical echography, the fineness of details (spatial resolution), the contrast of the image and the accuracy of the measurements depends on the frequency and focal distance of the ultrasonic probe, as well as the performances (geometry, extent, accuracy, speed) of the system for scanning the ultrasonic beam. The choice concerning the frequency and the focal distance of the probe depends on making a compromise concerning resolution and the penetration depth. In fact, owing to the increase of the attenuation of the ultrasonic waves with the frequency, the depth of penetration of the ultrasounds is much greater when the frequency is low. On the other hand, the resolution of the images reduces.

The accuracy of the measurements made on the image depend on the resolution, but also on the orientation of the ultrasonic beam with respect to the structure to be explored. In addition, the precision and reliability of an echographic examination are more important when the volume of the explored issue is large. Thus is the reason a 3D scanning adapted to the geometry of the explored organ allows a volume imaging of the structures, an improved definition of their contours and an accurate localisation of lesions.

In ophthalmology, the 2D echography at 10 MHz is used in current practice for exploring the anatomy and pathologies of ocular structures and more particularly those of the posterior pole (retina, optic nerve, vitreous table). The technique uses a sectorial scanning making it possible to obtain cutaway images (2D) with spatial resolutions close to one millimetre. Although sectorial scanning is not adapted to the bend of the cornea, an extremely rough examination of the entire anterior segment (cornea, iris, anterior chamber, crystalline lens) can however be obtained at 10 MHz. The use of higher frequencies, typically between 50 and 80 MHz, allows fine imaging of these structures.

Several systems functioning at 50 MHz (spatial resolution of 50 $\mu$m) have been highly developed.

The first, UBM (Ultrasound Backscatter Microscope) is a 2D echograph abler to explore in real time (eight images/s) with a linear scanning the structures of the anterior segment. The range of scanning is limited to a zone measuring 5 mm long and 5 mm deep. This limitation is due to the fact that the ultrasonic beam is only perpendicular to the central portion of the cornea. So as to produce an image of the entire cornea, it is necessary for the scanning to follow a curvilinear (or arciform) trajectory whose bending radius is close to the average bending radius of the cornea.

The patent application WO 01/49181 describes a system which carries out a scanning along a circular trajectory whose radius can be adjusted so as to approximately correspond to that of the eye of the patient.

This system includes two parallel rocker bars joined by one of their extremities to a structure for supporting the probe and by the other extremity to a rotating plate of a drive mechanism, the unit comprising the rocker bars, support structure and plate constituting an articulated parallelogram. These two rocker bars are joined by their central portion on a second plate identical to the first and coupled to the latter so as to rotate in synchronism with the latter. This rotation causes a translation movement of the rocker bars which remain parallel to an axis passing through the rotation centre of the two plates. The probe carries out a circular trajectory centered on said axis. During this rotation, the probe remains orientated towards the centre of the circular trajectory. An adjustment of the diameter of this trajectory can be obtained by varying by means of two cams the distance between the centres of rotation of the plates and the hinge pins of the rocker bars on these plates.

The drawback of this solution is that it only makes it possible to carry out circular trajectories of the probe and does not take account of the specific shape of the cornea.

Now the cornea is not really spherical and has large variations between its centre and the periphery: the further one is away from the centre of the cornea, the more the bending radius of the latter increases.

Figure 1:
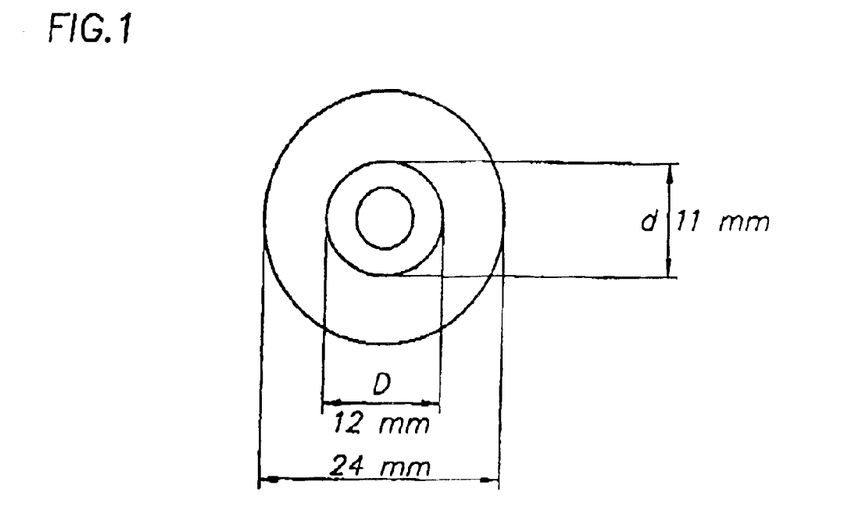
FIGS. 1 and 2 are diagrammatic representations, namely a top view (FIG. 1) and a cutaway view (FIG. 2) showing the shape of the cornea of an eye.
Figure 2:
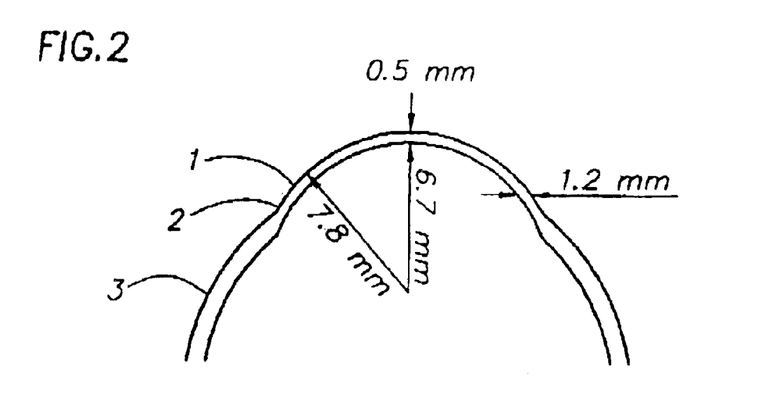

In fact, as shown on the accompanying FIGS. 1 and 2, the basic plane of the cornea 1 (eye seen from top) has an elliptical shape with a large diameter D of about 12 mm (perpendicular to the axis of the nose) and a small diameter d of about 11 mm (parallel to the axis of the nose), the difference of diameter originating from the opening and closing of the eyelids.

Moreover, it is a known fact that the cornea 1 has two zones, namely a central zone which is spherical (which corresponds approximately to the pupil area) and a peripheral zone in which the bending radius progressively increases towards the limbus. Thus, it appears that the cornea 1 is an aspheric and asymmetrical calvaria which progressively flattens towards its periphery. The average radius of the anterior face is about 7.8 mm and that of its posterior face is about 6.7 mm. The thickness at the centre of the cornea is about 0.5 mm and 1.2 mm at its periphery at the level of the limbus. Owing to the various bending radii between the cornea and the sclera 2, the joining point of the cornea 1 and the sclera 2 has a visible sulcus 3 (discontinuity) at the level of the irido-cornean angle.

In the rest of this text, the bending radius of the anterior face of the cornea shall be denoted by "the bending radius of the cornea".

By using a small keratometer, it has been observed that normal cornea exhibit flattening of 3 diopters or more at a distance of 2 to 3 mm from the cornean apex (region with the larger bend) which corresponds to a bending radius of 8.4 mm.

It has also been shown that the normal corneas are aspherical, more bent inward at the centre and exhibiting a progressive flattening towards their periphery. This flattening has an amplitude of 5 to 7 diopters, namely respectively a bending radius ranging from 8.8 to 9.5 mm which represents an increase varying from 12.8 to 21.7% with respect to the average bending radius of 7.8 mm (FIG. 2).

In particular, the further one is away from the centre of the cornea, the more the bending radius of the latter increases. The advantage of arciform scanning is to enable the probe to follow a trajectory whose bending radius is fixed and approximately equal to the average bending radius of the cornea, thus making it possible to have the axis of the ultrasonic beam orthogonal to a major portion of the surface of the cornea. However, this scanning shows several limitations at the periphery of the cornea where the ultrasonic beam no is longer strictly perpendicular to the cornea on account of the variation of the bending radius of the latter. In addition, even if a safety distance (for example 2 mm) is taken with respect to the anterior face of the cornea, because of the bending radius of the trajectory of the front face of the probe is [7.8+2=9.8 mm. As this bend is] smaller than that of the cornea of its periphery (which moves from 9 mm to 12 mm at the joining point with the sclera), the ultrasonic probe would tend to draw close to the sclera with a risk of contact (risk much bigger when the diameter of the probe is large).

OBJECT OF THE INVENTION

For this type of application, the aim of the invention is more particularly to embody a scanning system making it possible to move a probe along an arciform trajectory adapted to this increasing bending radius, (that is a curvilinear trajectory with a variable bending radius) whilst keeping the probe centered perpendicular to the cornea and/or the retina so as to improve the quality of the echographic signal received by the probe whilst ensuring that the latter does not approach the sclera and risking damaging the latter.

SUMMARY OF THE INVENTION

So as to achieve this result and similar results concerning other applications, the scanning system of the invention introduces a mechanism for activating an object, for example the probe implementing:

a first mobile structure driven in rotation by a first drive element around a first spin axis, a second mobile structure mounted rotating on the first mobile structure around a second axis parallel to the first and situated at a predetermined distance from the latter, a structure for supporting the object mounted rotating on the second structure around a third axis parallel to the second and situated at a predetermined distance from the latter, a first coupling element able to drive the second mobile structure in rotation around a second axis according to the movement of rotation of the first mobile structure around the first axis, a second coupling element distinct from the first and able to drive the structure supporting the object in rotation around a third axis according to the movement of rotation of the second mobile structure around the second axis.

The transmission ratios of the two coupling elements can be adjusted independent of each other.

Advantageously, the first coupling element could include a first pulley coaxial to the first axis and integral with the stator portion of the drive element, a second pulley coaxial to the second axis and integral with the second mobile structure, and a first belt, possibly notched, passing around said first and second pulleys.

The second coupling element could include a third pulley coaxial to the second axis and integral with the first mobile structure, a fourth pulley coaxial to the third axis and integral with the structure supporting the object, and a second belt, possibly notched, passing around said third and fourth pulleys.

The transmission ration of each of the coupling elements could possibly be modified by using pulleys having a different diameter, indeed even variable diameter pulleys of the type used in speed variators.

Moreover, so as to be able to carry out a three-dimensional scanning, the stator structure of the first drive means could be mounted rotating around a fourth axis orthogonal to the first three and be driven in rotation by second drive means.

By means of these arrangements, the scanning system of the invention is able to obtain:

a fast 2D and 3D arciform scanning during which the probe moves along a trajectory whose bending radius progressively varies according to the position of the probe from the cornean apex up to the cornea/sclera joining point, a compact scanning mechanism with a small spatial requirement, an exploration of the entire cornea, that is a cord able to reach 15 mm at a rate of eight images per second, an exploration of the retina, a high resolution ultrasonic imaging: focussed ultrasonic probes, frequency between 20 and 100 MHz, focal distance 6 to 27 mm, spatial resolutions from 15 to 100 $\mu$m, real time visualisation of digitised ultrasonic data.

BRIEF DESCRIPTION OF THE DRAWINGS

An embodiment of the invention appears hereafter, given by way of non-restrictive example with reference to the accompanying drawings on which.

DESCRIPTION OF THE PREFFERED EMBODIMENTS

The embodiment shown on these drawings consists of an ocular imaging device including an ultrasonic probe mounted on an activation mechanism so as to carry out an arciform scanning with a variable bending radius precisely adapted to the aspheric geometry of the cornea whilst allowing an exploration of the retina.

Figure 3:
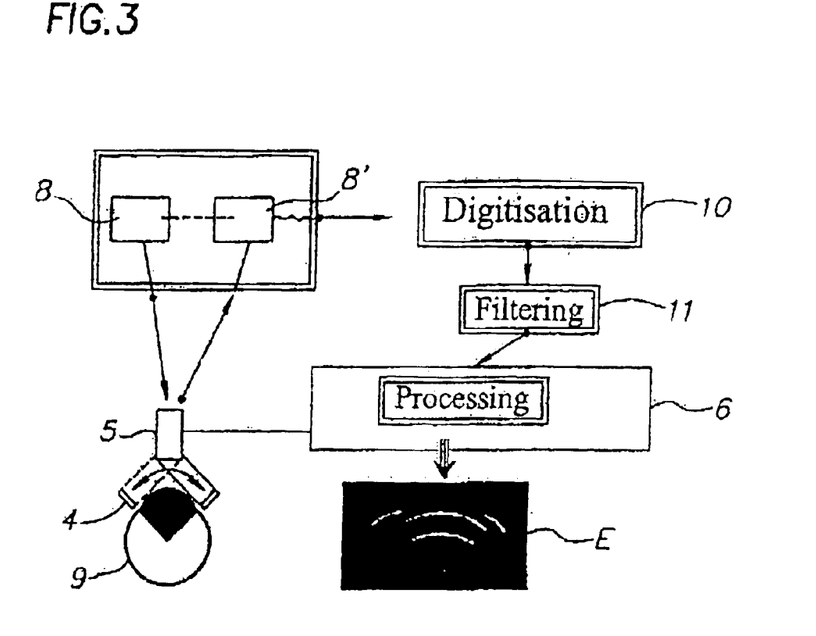
FIG. 3 is a synoptic diagram of an ocular echographic device.
Figure 4:
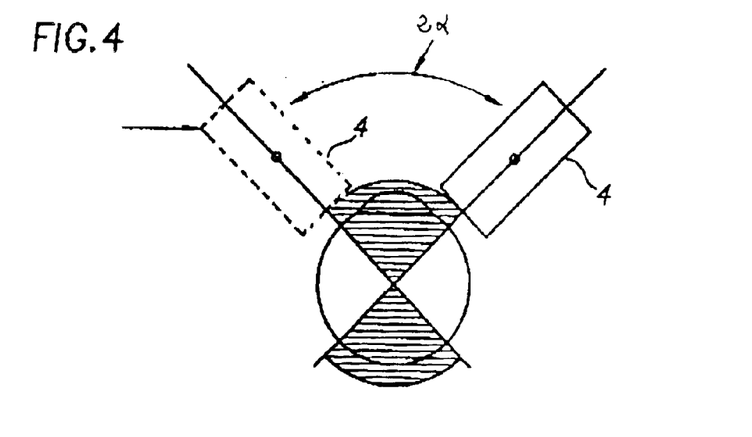
FIG. 4 is a diagrammatic axial cutaway view showing the "insonified" zones of an eye by an echographic probe.

As shown on FIG. 3, this device introduces a probe 4 borne by a scanning system 5 controlled by a processing unit 6.

This probe 4 includes a piezoelectric transducer which receives the electric pulses originating from a generator 8 and generates ultrasonic wave pulses in the direction of the cornea of an eye 9.

The ultrasonic waves reflected and/or diffused by the various media traversed by said ultrasonic waves are detected by the probe 4 which transmits corresponding electric signals to an amplifier 8' and a device successively carrying out digitisation (block 10), filtering (block 11) and processing (block 6) of these signals.

The processing unit 6, which consists here of a processor, then displays on a screen E two or three dimensions of the image of the zone scanned by the probe 4.

Figure 5:
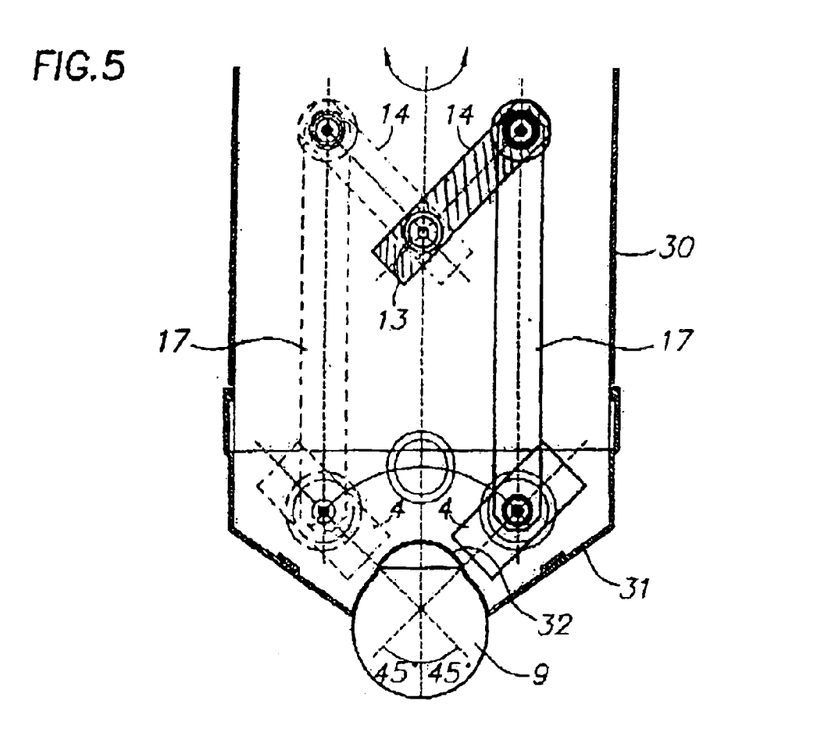
FIG. 5 is a diagrammatic cutaway view of a scanning system according to the invention.
Figure 6:
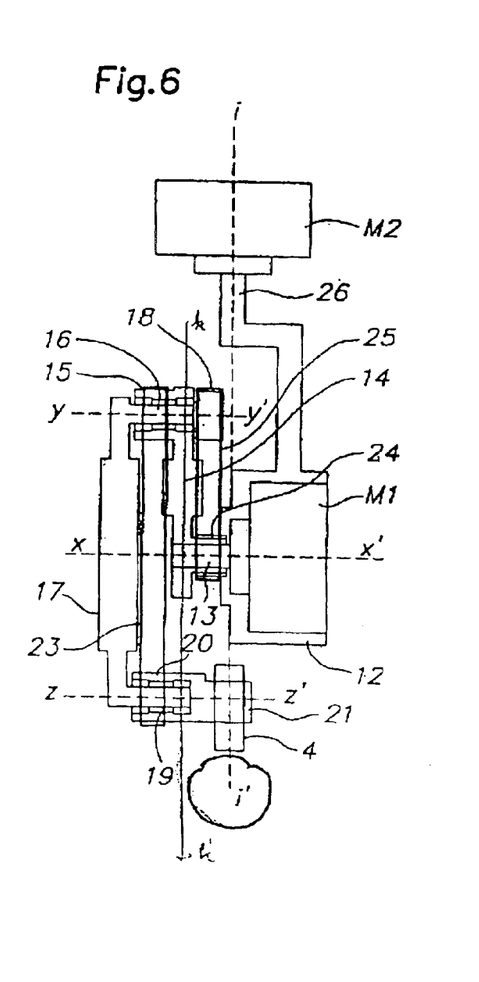
FIG. 6 is a front view of the scanning system shown on FIG. 5.
Figure 7:
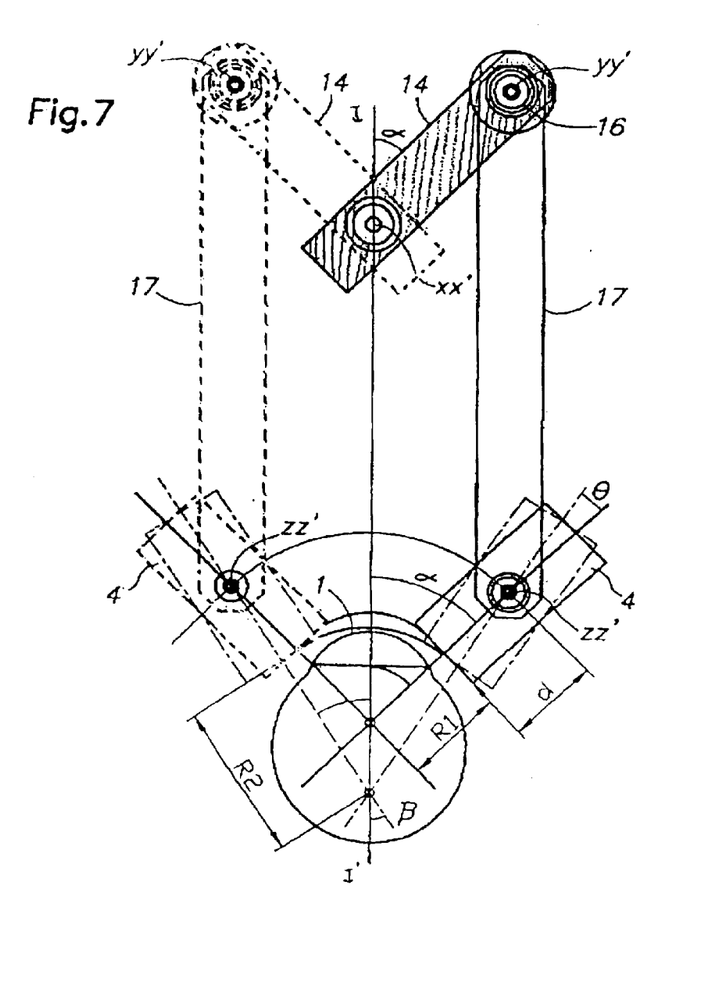
FIG. 7 is a partial schematic representation of the scanning system of FIG. 5 which illustrates the bending radius change principle.

As shown on FIGS. 5 to 7, the arciform scanning system used to move the probe introduces an electric step motor $M_1$ including a stator structure in which only one portion (the outer box 12) is visible, and a rotating drive shaft 13 to which one of the extremities of a rocker bar 14 is fixed, said bar extending perpendicular to the axis of rotation XX' of the shaft 13.

The other extremity of the rocker bar 14 bears a bearing 15 in which a shaft 16 is engaged fixed at a right angle on one extremity of a second rocker bar 17 and whose axis YY' is parallel to the axis XX'.

On the side opposite the rocker bar 17, the shaft 16 comes out of the bearing 15 and is shaped so as to have the form of a pulley 18.

The second rocker bar 17 bears at its other extremity a shaft 19 whose axis ZZ' is parallel to the axes XX' and YY'.

A bearing 20 integral with a support element 21 of the echographic probe 4 is engaged on the shaft 19.

The external faces of the bearings 15, 20 are placed opposite each other and are shaped so as to play the role of pulleys around which a belt 23, possibly notched, is placed.

Similarly, the shape of the pulley 18 situated at the extremity of the shaft 16 is placed opposite a tubular sleeves having the shape of a pulley 24 integral with the box 12 and which extends coaxially to a portion of the shaft 13. These two pulley forms 18, 24 are coupled to each other by a second belt 25, possibly notched.

The box 12 of the motor $M_1$ is borne by a structure integral with the drive shaft 26 of a second step motor $M_2$ whose axis II' extends normally to the axes XX', YY', ZZ' inside the scanning plane of the probe 4 (determined by the pivoting of the rocker bars 14, 17 around the axes XX', YY').

This second motor $M_2$, also controlled by the processor 6, is able to carry out a three-dimensional scanning.

Advantageously, the diameter of these pulleys could be different.

When this motor $M_2$ is inoperative and the drive shaft 13 of the motor $M_1$ rotates, the rocker bar 14 rotates around the axis XX' according to an angle a with respect to its initial position, principally with respect to the axis II' (figure 7). By way of example, this angle α could have a maximum value of 45° as shown on figure 5, but a larger clearance is possible.

Owing to the rotation of the rocker bar 14, the axis YY' describes a circular trajectory centered on the axis XX' and having as its radius the distance (centre distance of axes) between the axes XX' and YY', namely the centre distance length of the rocker bar 14.

This movement is transposed to the support element 21 of the ultrasonic probe 4 via the rocker bar 17. The belt 25 enables the shaft 16 to rotate with the same angle α as the shaft 13 (transmission ratio=1) and thus keep the rocker bar 17 still parallel to the axis II' irrespective of the angle α of the rocker bar 14 with respect to the axis II'.

Similarly, the belt 23 allows the pulley 20 to retain the same angle α and keep the support 21 of the probe 4 at the same angular position (even the angle α) as the rocker bar 14 with respect to the axis II'. Given the fact that the pulleys 15 and 20 have the same diameter, the support 21 of the probe 4 thus makes the same movement of rotation as the rocker bar 14.

Thus, the axis of rotation YY' describes a circular trajectory whose centre is the axis of rotation XX' and whose bending radius is the centre distance length of the rocker bar 14. The axis of rotation ZZ' describes the same trajectory as the axis YY', but its trajectory and its centre of rotation are offset downwards from the length of the centre distance of the rocker bar 17.

The probe 4 is fixed in its support 21 so that its axis is parallel to that of the rocker bar 14.

If the front face of the ultrasonic probe 4 describes a circle whose radius is close to the average bending radius of the cornea (generally given equal to 7.8 mm), the ultrasonic beam is then located at each point of its trajectory (or scanning) perpendicular to the surface of the cornea. When the angle α varies between −45° and +45°, the system makes it possible to scan the entire cornea and the sclera/cornea joining points (limbus).

The length of the rocker bar 14 determines the bending radius of the trajectory of the support 21 of the probe 4. The bending radius of the trajectory of the probe 4 can be modified by acting on the position of the probe 4 in its support 21 (distance d on FIG. 7) so that this trajectory can be adapted to the curve of the cornea and that of the retina (about 12 mm radius). By using a probes 4 having an appropriate focal distance, the system is capable of carrying out an extremely high resolution exploration of both the cornea and the retina.

Figure 8:
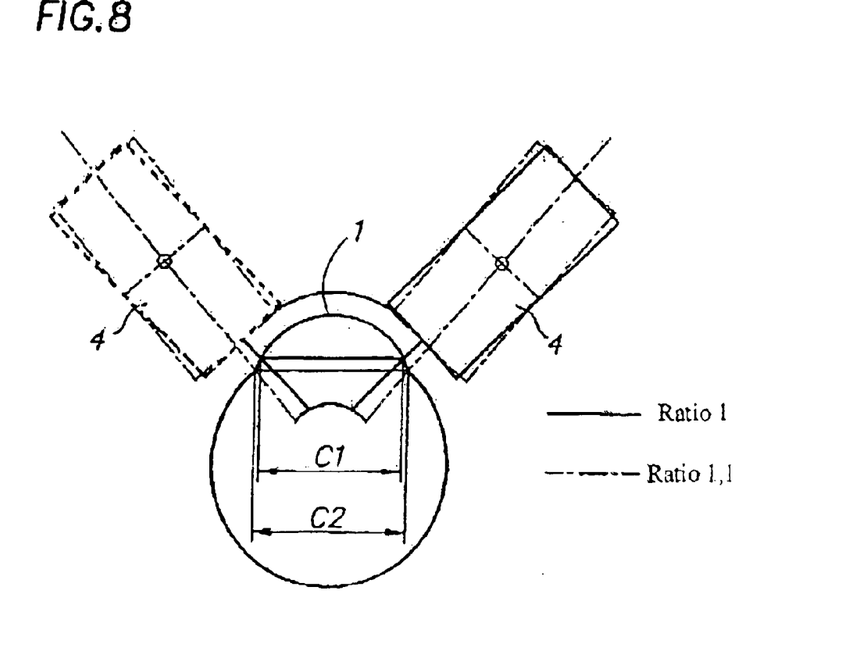
FIG. 8 is a diagrammatic representation showing the increase of the explored zone on the cornea by means of the system of the invention.

The modification of the ratio of the diameters of the pulleys 15 and 20 makes it possible to vazy the extent of the scanned zone. Thus it is possible to scan a larger zone on the cornea without modifying the mechanism generating the movement (FIG. 8). By taking 10 mm as a bending radius for the trajectory of the front face of the probe 4 and a maximum clearance of ± 45°, the chord length $C_1$ explored on the cornea is 11.5 mm with a unit pulley ratio and 13.2 mm with a pulley ratio of 1.1 (ligament $C_2$).

In addition, this modification makes it possible to keep the axis of the ultrasonic beam perpendicular to the cornea at any point, having regard to the fact that the cornea does not have the same bending radius at any point of its surface (the bending radius is smaller at the centre than at the periphery) by means of the progressive change of the orientation of the probe 4. With an arciform trajectory of the bending radius fixed equal to the average bending radius of the cornea, the axis of the ultrasonic beam is no longer strictly perpendicular to the cornea 1, especially at its periphery.

If the ratio of the diameters of the pulleys 15, 20 is no longer equal to 1 but equal to (1+k), then the axes of the probe 4 and of the rocker bar 14 are no longer parallel but exhibit between them an angle $\theta=\alpha.k$. The probe then exhibits an angle $\beta=\alpha.(1+k)$ with respect to the axis II' (FIG. 7).

When k is greater than 0, the angle β increases proportionally to α and the bending radius of the trajectory of the front face of the probe 4 reduces. So as to image the cornea, the bending radius of the trajectory of the front face of the probe 4 shall on the other hand increase when the cornea/sclera joining point is approached. As a result, k shall be negative and the pulley 20 shall have a diameter larger than that of the pulley 15.

In this case, when a increases, the bending radius of the trajectory of the front face of the probe 4 increases during scanning and the beam remains at any point perpendicular to the cornea. The system is thus able to have a scanning made whose bending radius varies according to the position of the probe 4 with respect to the centre of the cornea (FIG. 7). The ultrasonic beam becomes perpendicular to the surface of the cornea, especially at its periphery.

Generally speaking, the following formula is obtained:

$$R2 = \left((R1+d) \cdot \frac{\sin\alpha}{\sin\beta}\right) - d$$

Figure 9:
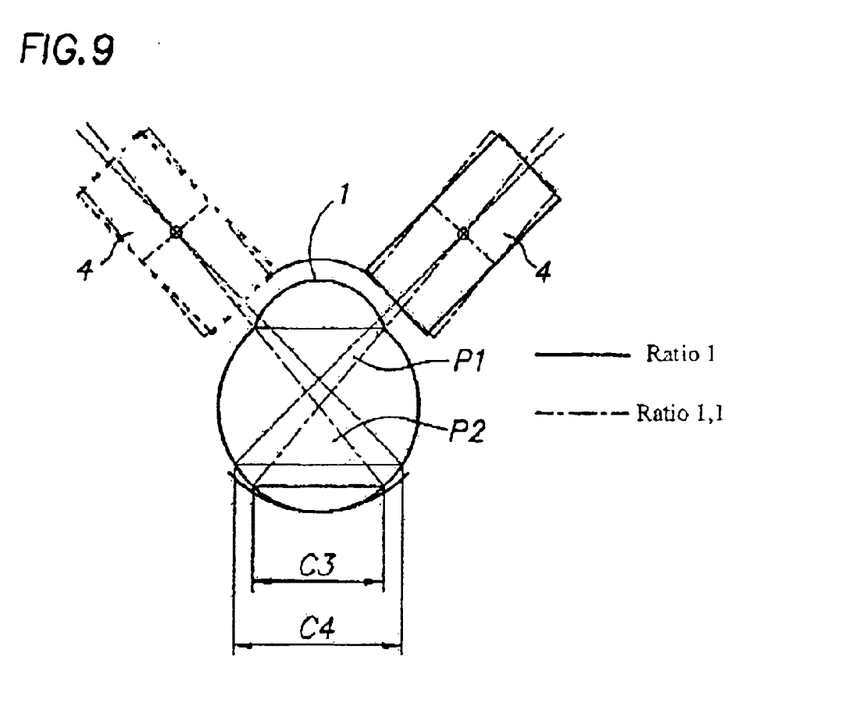
FIG. 9 is a diagrammatic representation showing the reduction of the explored zone on the retina.

With R1=bending radius for a ratio of diameters=1
R2=maximum bending radius for a ratio equal to 1+k By means of this arciform trajectory whose bending radius is not fixed but varies continually during scanning (diameter of pulleys 15 and 20 different), the scanning system of the invention is adapted to both imaging the cornea and the retina with a large field of exploration by keeping high frequency resolution (FIG. 9).

FIG. 9 is a representation showing the explored ligament $C_4$ of the retina 1 by the probe 4 for an identical diameter of the pulleys 15, 20 (axes shown by the broken lines) and for a diameter ratio of these pulleys equal to 1.1 (ligament $C_3$). When the ratio of the diameters of the pulleys 15 and 20 is equal to 1.1, the ligament $C_3$ explored with a probe 4 with a 25 mm focal distance is 16.18 mm on the retina. In addition, when the probe 4 is in an extreme scanning position (±45°), the incidence angle of the ultrasonic beam with respect to normal on the retina at this point is no longer only 2.4°. This therefore is almost perpendicular to the retina for the entire scanning making it possible to improve detection of the structure.

So as to carry out a 3D scanning of the structures of the cornea and the retina, the entire mechanical system previously described carries out a rotation by an angle varying from 0° to 180° around the axis II' with the aid of the motor $M_2$.

Advantageously, the motors $M_1$ and $M_2$ could consist of step motors controlled in programmable microsteps. By way of example, the rotational step can be equal to 0.032°. An optimum mechanical resolution of 20 μm (at the level of the cornea) makes it possible to carry out a 2D arciform scanning with a frequency of 8 Hz and a 3D scanning over 180° of a cornea with a 15 mm arc in less than 20 seconds.

All the elements of the scanning mechanism, the motors $M_1$, $M_2$, the ultrasonic probe 4 and its offset excitation module are housed in a tube 30 with for example a length of 20 cm and a diameter of 65 mm. These dimensions enable a clinic doctor to hold the device in his hand and obtain a controllable instrument.

The entire device is kept vertical with the aid of an articulated suspension arm (not shown). A mechanical system makes it possible to move and orientate the device along three degrees of freedom and to optimise the positioning of the probe with respect to the eye of the patient. In particular, the adjustment of the focussing of the ultrasonic beam on the cornea can be obtained via a manual vertical or motorised movement of the entire device.

So as to explore the eye, the patient is in an elongated position on the back (dorsal decubitus) and the device is brought closer using the flexible suspension arm and then positioned with the aid of the movement system to three degrees of freedom. Once the probe/cornea positioning is optimised, the device is kept in position so as to carry out a 3D exploration of the eye. The examined eye needs to remain still during the time of the examination. To achieve this, the patient could stare continuously at an optical test object.

A cup 31 (FIG. 5) is secured to the tube 30 so as to allow an immersion mode examination. The cup 31 contains the coupling liquid required for the propagation of the ultra-sounds and protects the eye from the movements of the probe 4. The shape of this cup is selected so that it makes it possible to retain a safety distance between the eye and the probe 4. It is transparent and enables the clinic doctor to visually control the distance between the probe and the eye.

Secured to this cup 31 is a transparent membrane 32 made of a material which does not attenuate the high frequency ultrasounds. This fine, resistant, flexible and impervious membrane 32 confines the coupling liquid whilst being able to protect the eye from any risk of viral contamination and any accidental contact with possible mechanical elements.

Both the membrane and the cup are made of biocompatible materials.

The focussing of the ultrasonic beam on the structures of the eye is directly controlled on the image. Software protection is provided making it possible to stop scanning should an echo be detected indicating that the cornea is too close to the probe. The time (delay) position of the echo of the cornea is detected at any moment and the displacement motors are stopped as soon as the probe/cornea distance reaches a certain threshold (2 mm for example). A sound alarm can also accompany the stoppage of the motors so as to warn the operator.

The high resolution exploration of the cornea, the epithelium and the tissues of the anterior segment is effected with a high frequency probe (50 to 100 MHz) with a short focal distance (6 to 10 mm).

The exploration of the retina and the structures of the posterior pole $P_2$ can be made with a probe having a frequency ranging between 10 and 50 MHz whose focal distance varies between 25 and 30 mm. By using a high frequency probe with a longer focal distance and by varying the probe/eye distance, it is possible to carry out a 3D high resolution of, not only the retina, but also a portion of the cornea and the anterior chamber $P_1$.

By way of example, the ultrasonic probe 4 could be excited by a receiver/transmitter 8, 9 with a wide passband (100–200 MHz). The radiofrequency signals reflected by the tissues are digitised by the digitisation card (block 10) capable of functioning up to a sampling frequency of 500 MHz with a resolution of 8 bits. The processor 6 records the digitised data and then calculates so as to display the images. A software programme installed in the processor 6 is able to parameterise the 2D and 3D grabbings and the various cards present on the machine and then process the information so as to make a 2D and 3D display.

By scanning the entire cornea arc, it is thus possible to obtain an image of a section of the cornea simultaneously showing the two iridocornean angles. By then acting on the rotation motor, it is possible to acquire various sections over the entire perimeter of the cornea and thus obtain three-dimensional information. All the grabbing and calculation procedures have been optimised for a real-time imaging. The system can embody eight sections per second and a full scanning of the cornea in less than 20 seconds.

By using image processing algorithms specific to the grabbed data, it is possible to reconstruct the contours of the structures and represent volume images and 3D quantitative information. The cartography of the thickness of the cornea (useful for the control of laser refractive surgery), the measurement of the volume of the anterior chamber $P_1$ (follow up of glaucoma) and the follow up of the evolution of the volume and morphology of the tumours of the anterior segment and the posterior pole $P_2$ are possible using the open-ended system.

In addition to high-precision volume biometry, the high frequency digitisation of the ultrasonic signal and its frequency exploration using specific algorithms for processing the signal make it possible to have the pathological tissues characterised by the acoustic parameters (attenuation and backscattering of the ultrasounds).

The previously described system thus allies speed and precision and makes it possible to 2D and 3D explore wide zones (limb-to-limb at the level of the anterior segment). It is able to display the structures of the anterior segment and also those of the posterior pole $P_2$ and has the following advantages:

this system is able to carry out an arciform scanning whose bending radius progressively varies according to the position of the ultrasonic probe with respect to the centre of the cornea which makes it possible to get rid of the problem of loss of signal observed on current devices and have a perfect imaging of the entire cornea (observance of the aspheric geometry of the cornea). This system is also able to have better exploration of the retina than the case with current devices.

This system is compact, manageable, occupies less space and is flexible and open-ended.

It has three degrees of freedom making it possible to move and position the probe with respect to the eye.

An examination can be conducted in an elongated position: by means of using the transparent, sealed and biocompatible cup 31 and membrane 32, the eye is visible by the clinic doctor who is able to visually control the position of the eye with respect to the probe. For the patient, this examination is simple and causes no particular distress.

What is claimed is:

1. System for moving an object along an arciform trajectory with a variable bend, said system comprising:
    a first mobile structure driven in rotation by a first drive element around a first axis of rotation,
    a second mobile structure mounted rotating on said first mobile strucure around a second axis parallel to the first and situated at a predetermined distance from the latter,
    a structure for supporting the object mounted rotating on the second structure around a third axis parallel to the second and situated at a predetermined distance from the latter,
    a first coupling element able to move said second mobile structure in rotation around said second axis according to the movement of rotation of said first mobile structure around said first axis,
    a second coupling element distinct from the first and able to move the structure supporting the object in rotation around said third axis according to the movement of rotation of said second mobile structure around said second axis.
    said drive element having a strator structure which is mounted rotating around a fourth axis orthogonal to said first, second and third axis.

2. System according to claim 1, wherein the transmission ratio of at least one of said coupling elements is adjustable.

3. System according to claim 1, wherein said first drive element cmprises a stator portion and said first coupling element comprises a first pulley coaxial to said first axis and integral with said stator portion, a second pulley coaxial to said second axis and integral with said second mobile structure and a first belt, passing around said first and second pulleys.

4. System according to claim 1, wherein said second coupling element comprises a third pulley coaxial to said second axis and integral with said first mobile structure, a fourth pulley coaxial to the third axis and integral with the structure bearing the object, and a second belt, possibly notched, passing around said third and fourth pulleys.

5. System according to claim 1, wherein at least one of said coupling elements comprises pulleys having different diameters.

6. System according to claim 1, wherein at least one of said coupling elements comprises pulleys having a variable diameter.

7. System according to claim 1, wherein said stator structure is driven in rotation by second drive element.

8. System according to claim 1, wherein said object consists of an ocular echographic probe.

9. System according to claim 8, wherein said arciform trajectory is adapted to the shape of the cornea of an eye and in that said probe is kept centered perpendicular to the cornea and/or the retina of this eye.

10. System according to claim 8, said probe comprising a piezoelectric transducer which receives electric pulses derived from a generator and which generates ultrasonic waves, and in that said waves reflected and/or diffused by the various mediums traversed by the ultrasonic waves are detected by the detection means of the probe which transmit corresponding electric signals to an amplifier and a circuit successively carrying out a digitisation, a filtering and a processing of the signals before being applied to a processor which carries out a displaying of the image scanned by the probe.

11. Ocular echographic system for moving an ocular echographic probe along an arciform trajectory with a variable bend located near or the cornea of an eye of a patient, said system comprising:
    a first mobile structure driven in rotation by a first drive element around a first axis of rotation,
    a second mobile structure mounted rotating on said first mobile structure around a second axis parallel to the first and situated at a predetermined distance from said first axis,
    a structure for supporting the object mounted rotating on the second structure around a third axis parallel to the second and situated at a predetermined distance from said second axis,
    a first coupling element able to move said second mobile structure in rotation around said second axis according to the movement of rotation of said first mobile structure around said first axis,
    a second coupling element distinct from the first and able to move the structure supporting the ocular echographic probe in rotation around said third axis according to the movement of rotation of said second mobile structure around said second axis.

12. System according to claim 11, wherein the transmission ratio of at least one of said coupling elements is adjustable.

13. System according to claim 11, wherein said first drive element comprises a stator portion and said first coupling element comprises a first pulley coaxial to said first axis and integral with said stator portion, a second pulley coaxial to said second axis and integral with said second mobile structure and a first belt, passing around said first and second pulleys.

14. System according to claim 11, wherein said second coupling element comprises a third pulley coaxial to said second axis and integral with said first mobile structure, a fourth pulley coaxial to the third axis and integral with the structure bearing the object, and a second belt, possibly notched, passing around said third and fourth pulleys.

15. System according to claim 11, wherein at least one of said coupling elements comprises pulleys having different diameters.

16. System according to claim 11, wherein at least one of said coupling elements comprises pulleys having a variable diameter.

17. System according to claim 11, wherein said first drive element comprises a stator structure of said first drive element is mounted rotating around a fourth axis orthogonal to said first, second and third axes so that a 3D scanning is carried out.

18. System according to claim 11, wherein said stator structure is driven in rotation by second drive element.

19. System according to claim 11, wherein said arciform trajectory is adapted to the shape of the cornea of an eye and in that said ocular echographic probe is kept centered perpendicular to the cornea and/or the retina of this eye.

20. System according to claim 11, said ocular echographic probe comprising a piezoelectric transducer which receives electric pulses derived from a generator and which generates ultrasonic waves, and in that said waves reflected and/or diffused by the various mediums traversed by the ultrasonic waves are detected by the detection means of the ocular echographic probe which transmit corresponding electric signals to an amplifier and a circuit successively carrying out a digitisation, a filtering and a processing of die signals before being applied to a processor which carries out a displaying of the image scanned by the ocular echographic probe.

* * * * *